United States Patent [19]

Sternby

[11] Patent Number: 5,024,756
[45] Date of Patent: Jun. 18, 1991

[54] DIALYSIS SYSTEM AND METHOD THEREFOR

[75] Inventor: Jan P. Sternby, Lund, Sweden

[73] Assignee: Gambro AB, Sweden

[21] Appl. No.: 316,999

[22] Filed: Feb. 28, 1989

[30] Foreign Application Priority Data

Mar. 3, 1988 [SE] Sweden ............................... 8800757

[51] Int. Cl.$^5$ ........................ B01D 61/32; B01D 63/00
[52] U.S. Cl. ...................................... 210/93; 219/96.2; 219/206; 219/321.72; 219/647
[58] Field of Search ............. 210/93, 96.2, 206, 321.6, 210/321.65, 321.71–321.81; 604/4, 5, 6

[56] References Cited

U.S. PATENT DOCUMENTS

| | | | |
|---|---|---|---|
| 4,293,409 | 10/1981 | Riede et al. ..................... | 210/321.71 |
| 4,508,622 | 4/1985 | Polaschegg et al. ............... | 210/96.2 |
| 4,844,871 | 7/1989 | Polaschegg ..................... | 210/321.6 |

*Primary Examiner*—W. Gary Jones
*Attorney, Agent, or Firm*—Lerner, David, Littenberg, Krumholz & Mentlik

[57] ABSTRACT

A dialysis system and method is based upon a comparison of the value of a parameter being measured of the dialysis liquid after the dialyzer with a set value of the corresponding parameter being controlled before the dialyzer. Based upon this comparison, a measure of the dialysis performed is obtained, and with the assistance of this measured value, as well as the knowledge of other factors, for example, adjusted values relevant for the analysis, conditions of the patient's blood can be determined theoretically and thereby controlled.

16 Claims, 1 Drawing Sheet

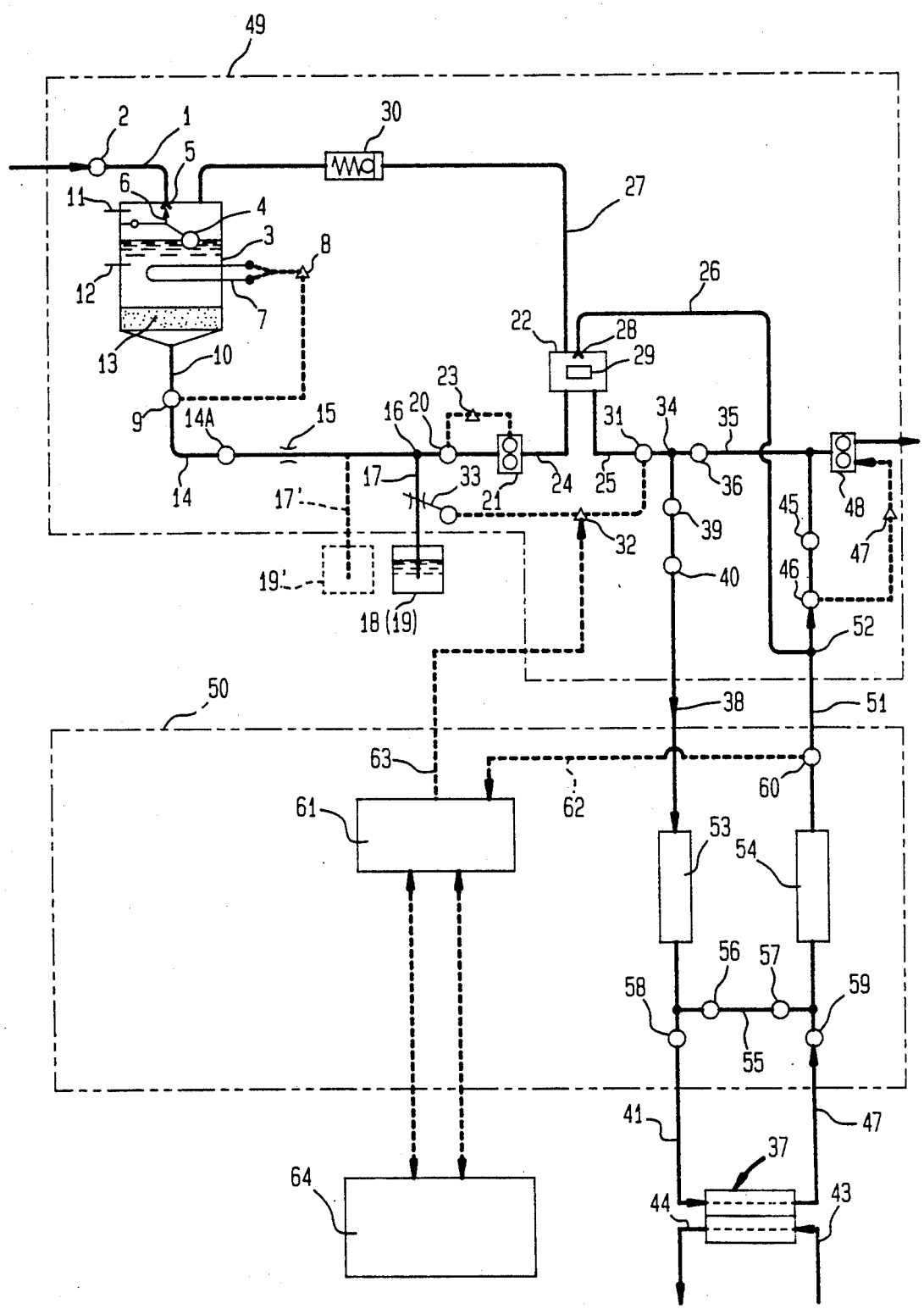

DIALYSIS SYSTEM AND METHOD THEREFOR

BACKGROUND OF THE INVENTION

The present invention relates in general to a dialysis system and method therefor, and more particularly, to such a system and method which compares the value of a measured parameter of the dialysis liquid, e.g., conductivity, blood gases, temperature, pH, and the like, at a location after the dialyzer with a non-measured predetermined set value of the parameter before the dialyzer, whereby the corresponding parameter of the blood of a patient can be theoretically determined and thereby controlled.

In known dialysis systems and treatments, there is generally no feedback of the patient's blood parameters, e.g., temperature, blood gases, electrolyte content, etc., to the dialysis machine. Thus, the value of these patient parameters may become abnormal during the dialysis process without any corrective interaction by the dialysis machine, as long as the dialysis machine is being maintained at the correct parameter set value. Examples of dialysis systems which control the composition of the dialysis liquid irrespective of these blood parameters of the individual patient are known from U.S. Pat. Nos. 4,158,034, 4,293,409 and 4,508,622. Other known dialysis systems are disclosed in U.S. Pat. Nos. 4,194,974, 4,191,359, 4,585,552, 4,536,201, 4,762,618, 4,728,496, and 4,797,655, and European Patent Publications Nos. EP B 22 922 and EP A 204 260.

In U.S. Pat. No. 4,508,622, a dialysis system is disclosed which includes a first detector mounted upstream of the dialyzer and a second detector mounted downstream of the dialyzer by means of which the composition of the dialysis solution can be regulated. The actual measured data of the dialysis liquid from these two detectors are compared and eventually used to control the composition of the dialysis solution. This dialysis system is difficult to control due to the necessity of having to compare two continuously varying measured parameter values before and after the dialyzer.

SUMMARY OF THE INVENTION

It is one object of the present invention to increase the comfort of a patient during dialysis by individualizing the dialysis treatment. This is achieved by measuring and adopting certain of the patient's blood parameters to control the dialysis machine and thus, the dialysis treatment on an individualized basis. Examples of a patient's blood parameters may include blood pressure, temperature, blood gas content, electrolyte content, pH-status, and the like. These measurements are made without contact with the patient's blood, so that transmitters and other sensors used need not be constructed of the disposable type or require sterilization between each treatment.

The dialysis system in accordance with one embodiment of the present invention includes means for comparison of the parameter being measured after the dialyzer with the set value of the corresponding parameter before the dialyzer. Through this comparison, a measure of the dialysis performed is obtained, and with the assistance of this measure, as well as the knowledge of other factors, e.g., adjusted values relevant for the analysis, conditions of the patient's blood can be determined theoretically and thereby controlled.

In accordance with the present invention, there is provided means for using the comparative value measured for calculating the corresponding blood parameter, which is thereby altered as a function of the parameter measured, for the purpose of the calculation and/or control of the blood parameter of the patient. The comparative value of the parameter measured is thus used for the direct control of the composition of the dialysis liquid, and thereby, an indirect passive control of the composition of the patient's blood.

With respect to the electrolyte composition of a patient's blood, it is generally required to obtain the value of same by measuring the conductivity of the dialysis liquid after passing through the dialyzer. As a result of the influence of the patient's blood on the dialysis liquid, the conductivity of the incoming dialysis liquid will be altered and the magnitude of the alteration will be dependent upon the composition of the patient's blood. Since this conductivity is generally produced by sodium ions together with its anions, the conductivity largely becomes a measure of the sodium content in the dialysis liquid and in the patient's blood. Preferably, the dialysis system in accordance with the present invention is provided with a conductivity meter arranged after the dialyzer for measuring the conductivity of the dialysis liquid for the purpose of calculation and/or control of the conductivity and/or the sodium content in the patient's blood.

In accordance with another embodiment of the dialysis system of the present invention, there is provided one or more ion-selective electrodes for measuring the content of one or more defined ions in the dialysis liquid for the purpose of calculation and/or control of the corresponding ion content in the patient's blood. In this manner, other ions besides sodium can also be measured, for example, calcium ions and potassium ions.

It should be understood that many other blood parameters can be calculated and/or controlled with the assistance of the corresponding values measured on the dialysis liquid side. Thus, it is contemplated, for example, to provide the dialysis system with a gas analyzer arranged after the dialyzer for measuring the gas content of the dialysis liquid for the purpose of calculation and/or control of corresponding blood gases.

The dialysis system in accordance with the present invention is provided with means for the control of the composition of the dialysis liquid before the dialyzer as a function of the parameter measured in such a manner that the dialysis result becomes a direct function of the corresponding blood parameter in the patient. As a result, conditions on the blood side of the dialyzer will be directly determined from the dialysis and not the preset values on the dialysis liquid side. If the dialysis system in accordance with the present invention is adapted for determination of the conductivity and/or the sodium content in the patient's blood, the above means for adjusting the composition of the dialysis liquid before the dialyzer can be adapted to bring about an equilibrium between the conductivities in the dialysis liquid and in the patient's blood. In this manner, a conductivity adapted to the individual is obtained which will provide maximum comfort for the patient.

The dialysis system in accordance with the present invention may include measuring devices for measuring the actual dialysis liquid parameter before and after the dialyzer. The dialysis system may also be provided with a shunt line for conducting the fresh dialysis liquid past the dialyzer directly to the measuring device normally placed after the dialyzer, for the purpose of calibration of the measuring devices used. It should be noted that any minor fault common to both measuring devices is of less importance to the final result than if only one of the measuring devices were to provide an incorrect measured value.

In accordance with one embodiment of the present invention, there is provided a dialysis system constructed of a dialyzer having (i) a dialysis liquid input side and a dialysis liquid output side for the flow of dialysis liquid therethrough, and (ii) a blood input side and a blood output side for the flow of blood therethrough, control means for controlling one or more parameters of the dialysis liquid at a desired control value on the dialysis liquid input side of the dialyzer, measuring means for measuring the value of at least one of the parameters of the dialysis liquid on the dialysis liquid output side of the dialyzer, and comparison means for comparing the value of the measured parameter with the desired control value of the corresponding parameter being controlled by the control means.

In accordance with another embodiment of the present invention, there is provided a dialysis method comprising the steps of a dialyzer having (i) a dialysis liquid input side and a dialysis liquid output side for the flow of dialysis liquid therethrough, and (ii) a blood input side and a blood output side for the flow of blood therethrough, the method constructed of controlling one or more parameters of the dialysis liquid at a desired value on the dialysis liquid input side of the dialyzer, measuring the value of at least one of the parameters of said dialysis' liquid on the dialysis liquid output side of the dialyzer, and comparing the value of the measured parameter with the desired value of the corresponding parameter being controlled by the control means.

BRIEF DESCRIPTION OF THE DRAWINGS

The above description, as well as further objects, features and advantages of the present invention will be more fully understood with reference to the following detailed description of a presently preferred, but nonetheless illustrative, dialysis system and method therefor, when taken in conjunction with the accompanying sole drawing, wherein there is shown a block diagram of the dialysis system constructed of a mixing module, a flow control module, an external computer and a dialyzer.

DETAILED DESCRIPTION

It is to be understood that the term dialysis system, as used herein, also contemplates and embraces other systems for similar treatments, for example, haemodiafiltration, that is, dialysis with such high ultrafiltration that a certain quantity of replacement liquid has to be supplied to the patient to make up for the filtrate removal.

Referring to the sole drawing, an inlet duct for fresh water is designated by numeral 1. The inlet duct 1, which is provided with an inlet valve 2, leads to a water vessel 3. Vessel 3 is provided with a float valve 4 which is adapted to close the water intake with the assistance of a closing cone 6 when the water vessel has been filled. The water vessel 3 includes heating means 7 for heating the contained water, e.g., in the form of a heating loop. The heating loop is controlled by a temperature regulator 8, which in turn, is controlled by a temperature transmitter 9 arranged in the outlet duct 10 from the vessel 3. Vessel 3 includes maximum and minimum monitors 11 and 12 for sensing the liquid level in the vessel. These level monitors 11 and 12 may be adapted, for example, to directly control the inlet valve 2. The vessel 3 also contains a filter element 13 which is intended to remove all solid particles from the water, but which also removes a certain amount of gas from the water, e.g., free gas bubbles.

The heated fresh water from vessel 3 is conducted via the outlet duct 10, the temperature transmitter 9, a duct 14 having a shut-off valve 14a, and a throttle valve 15, to a branching point 16. Connected to point 16 is a duct 17 which normally feeds from a source 18 of salt solution concentrate. Generally, source 18 may be a drum containing a salt solution. When the dialyzer system shown is to be sterilized, however, this drum is replaced by one containing a sterilizing agent which is designated by reference numeral (19) in the drawing. It is also contemplated to connect a further duct 17' to the dialysis system parallel with duct 17 for the connection of a separate vessel 19', as indicated in the drawing by broken lines.

From point 16, the fresh dialysis liquid flows via pressure gauge 20 and pump 21 to a bubble separator 22. The pressure gauge 20 controls pump 21 via a pressure regulator 23. The supply line to the bubble separator 22 is designated by reference numeral 24. From the bubble separator 22, there is provided a dialysis liquid supply line 25, a line 26 for the removal of the separated gases, and a return line 27. The inlet 28 to the gas separator line 26 is controlled by a float valve 29 which closes this inlet when the bubble separator 22 is filled with liquid in connection with sterilization. The return line 27 is provided with a spring-loaded check valve 30 and returns to the liquid vessel 3.

The dialysis liquid supply line 25 connects to, for example, a conductivity meter 31 which via a controller 32, controls a throttle valve 33 provided in duct 17 for the salt solution concentrate. Alternatively, it may control a concentrate pump (not shown) in the same duct 17. After the conductivity meter 31, the liquid flow reaches a further branching point 34 from which originates shunt line 35 having a valve 36. The shunt line 35 is used when it is desired to couple the dialysis liquid flow past the dialyzer, e.g., when an abnormality is detected in the dialysis liquid, for example, its temperature or salt content. Normally, the dialysis liquid will flow to the dialyzer 37 via a line 38 which contains a valve 39 and a flow meter 40. On the way to the dialyzer 37, the dialysis liquid passes a flow control module which, as a whole, is designated by reference numeral 50. The components described up to now, on the other hand, are included in a liquid preparation module which, as a whole, is designated by reference numeral 49. On the way from the dialyzer 37, the dialysis liquid once again passes the flow control module 50 to be returned via a line 51 to the module 49. At a point 52, the line 51 is coupled together with the line 26 from the bubble separator 22.

The lines or tubings which are normally coupled to the dialyzer 37 are designated 41. During sterilization, these lines or tubings are coupled to a safety-bypass (not shown), for example, as described in U.S. Pat. No. 4,122,010. The inlet and outlet respectively on the blood side of the dialyzer 37 are designated by reference numerals 43 and 44.

A blood detector 45, provided in the module 49, provides an alarm which shuts down the whole dialysis system if blood is detected in the dialysis liquid. This blood detector 45, for example, may be transparent tubing opposite an otherwise shielded photocell device which directly senses the presence of any blood in the dialysis liquid. Before the blood detector 45, a pressure gauge 46 is provided, which via a controller 47, controls a liquid pump 48. Thereafter, the dialysis liquid flow is conducted to a drain (not shown).

In the module 50 the dialysis liquid flow to the dialyzer 37 is measured by a first measuring device 53. In the same manner, the dialysis liquid flow from the dialyzer 37 is measured by a second measuring device 54. Through a comparison of the values obtained, the ultrafiltration in the dialyzer 37 can be determined. The two measuring devices 53 and 54 may be included, for example, in a differential measuring arrangement of the type which is described in British Patent 2,003,274 or in U.S. Pat. No. 4,585,552. During the calibration of the measuring devices 53 and 54, the dialyzer 37 is shunted by a bypass line 55 which includes two valves 56 and 57. At the same time, the lines to and from the dialyzer 37 are shut off by valves 58 and 59 respectively.

After the dialyzer liquid flow has passed through the measuring device 54, it passes through a device 60 for the measurement of at least one of its parameters, e.g., electrolyte content. In the example shown, the device 60 includes a conductivity meter. The value of the parameter measured in transmitted to a microprocessor 61, which is indicated by the broken line 62. The measured value is compared with the actual set value of the same parameter before the dialyzer 37, that is, conductivity. This set value is adjusted with the assistance of the microprocessor 61 which is indicated by broken line 63. This takes place with the assistance of the aforementioned control means 32. If desired, the microprocessor 62 may be provided with data from or may furnish data to a further personal computer 64. As a result, the individual parameter values of the patient can be transferred to the microprocessor 61 at the same time as the values calculated for the blood side of the dialyzer are determined.

It is generally preferred to measure directly various ions with the assistance of ion-selective transmitters instead of using a conductivity meter. In this regard, a conductivity measurement is appreciably more stable, more accurate, simpler and less expensive. Preferably, one conductivity meter is used. It is intended in accordance with the present invention to measure the conductivity on the dialysis liquid side by device 60 so as to calculate, theoretically, the conductivity on the blood side. Based upon the assumption that the conductivity is largely dependent upon the sodium content, the sodium passage or sodium dialysance is determinative of the effect on the blood conductivity in response to the conductivity value of the dialysis liquid measured after the dialyzer. A mass balance for sodium at constant flow and neglecting the so-called Donnan effect, results in the formula:

$$Cd_{out} = Cd_{in} + (Cb_{in} - Cd_{in}) \times K$$

wherein
 $Cd_{out}$ = the conductivity or the concentration of sodium in the used dialysis liquid.
 $Cd_{in}$ = the conductivity or the concentration of sodium in the fresh dialysis liquid.
 $Cb_{in}$ = the conductivity or the concentration of sodium in the untreated blood.
 K = proportionality constant depending on the flow rate.

If the ultrafiltration is kept at zero, K becomes $D1/Qd$ (= relative dialysance) where D1 = dialysance value for sodium/conductivity.
 Qd = dialysis liquid flow.

The above formula applies also where the ultrafiltration is different from zero, but with a modified value of K. When the factor K is known, and by measuring $Cd_{out}$, it is possible to calculate $Cb_{in}$, if at the same time $Cd_{in}$ is set to equal the set value of the corresponding parameter.

The factor K can be determined by two different approaches. The first approach starts out with a knowledge of the dialyzer, blood flow rate and liquid flow rate, so as to determine the factor K empirically. It is also possible, in accordance with a second approach, to determine the factor K continuously by a regular predetermined change of the set conductivity of the dialysis liquid. At each change, a measure of the factor K is obtained from a comparison between the desired conductivity before and the measured conductivity after the dialyzer. This method employs a liquid conductivity which, during the dialysis treatment, is altered by incremental steps, e.g., every sixth minute by 0.5 mS/cm, up or down respectively from the set value, which may be in the order of magnitude of from about 13.7 to 14.0 mS/cm. These changes are so rapid, that the patient's body most likely will not keep up with them to any appreciable extent. At the same time, they are so small that they do not notably affect the aforementioned formula.

It is to be understood that the invention is not limited solely to the embodiments described above, but can be varied within the framework of the subsequent claims. For example, the dialysis system in accordance with the above described embodiment is based on only one concentrate, that is taken from the container 18. The present invention also may be applied when two concentrates are used. The parameter value measured in device 60 is compared in this case with a ready-mixed dialysis liquid, that is, after the addition of the two concentrates being used. The two concentrates need not be in liquid form, but may also be used in powder form.

Although the invention herein has been described with references to particular embodiments, it is to be understood that these embodiments are merely illustrative of the principles and application of the present invention. It is therefore to be understood that numerous modifications may be made to the embodiments and that other arrangements may be devised without departing from the spirit and scope of the present invention as defined by the claims.

I claim:

1. A dialysis system comprising a dialyzer having (i) a dialysis liquid input side and a dialysis liquid output side for the flow of a dialysis liquid therethrough, and (ii) a blood input side and a blood output side for the flow of blood therethrough, control means for controlling one or more parameters of the dialysis liquid at a non-measured desired set value on the dialysis liquid input side of said dialyzer, measuring means for measuring the value of at least one of said parameters of said dialysis liquid on the dialysis liquid output side of said dialyzer, and comparison means for comparing the value of the measured parameter with the non-measured desired set value of the corresponding parameter being controlled by said control means.

2. The dialysis system in accordance with claim 1, further including means for adapting the value of the measured parameter for the calculation and/or control of a corresponding blood parameter, said blood parameter being altered as a function of the value of the measured parameter of the dialysis liquid.

3. The dialysis system in accordance with claim 1, wherein said measuring means comprises a conductivity meter for the measurement of the conductivity of the dialysis liquid for the calculation and/or control of the conductivity in the blood.

4. The dialysis system in accordance with claim 3, wherein said conductivity of the blood corresponds to the sodium ion content thereof.

5. The dialysis system in accordance with claim 3, wherein the conductivity of the blood is calculated according to the formula:

$$Cd_{out} = Cd_{in} + (Cb_{in} - Cd_{in}) \times K$$

wherein:
- $Cd_{out}$ = the measured conductivity or concentration of ions in the dialysis liquid,
- $Cd_{in}$ = the desired conductivity or concentration of ions in the fresh dialysis liquid,
- $Cb_{in}$ = the conductivity or concentration of ions in the untreated blood, and
- $K$ = a proportionality constant.

6. The dialysis system in accordance with claim 5, wherein said ions are selected from the group consisting of sodium ions, potassium ions, and calcium ions.

7. The dialysis system in accordance with claim 5, wherein the factor K is determined by incrementing the desired value of the conductivity of the dialysis liquid, a constant amount, from an initial value in the order of magnitude of from about 13.7 to 14.0 mS/cm, wherein after each increment of the desired value the factor K is determined from a comparison between the desired conductivity on the dialysis liquid input side and the conductivity measured on the dialysis liquid output side of the dialyzer.

8. The dialysis system in accordance with claim 5, wherein the factor K is determined empirically as a function of at least the blood flow rate and the liquid flow rate through said dialyzer.

9. The dialysis system in accordance with claim 5, wherein the factor K corresponds to the formula D1/Qd;
wherein:
- D1 = the dialysance value for the conductivity of the dialysis liquid, and
- Qd = the flow rate of the dialysis liquid.

10. The dialysis system in accordance with claim 1, wherein said measuring means comprises an ion-selective electrode for the measurement of the content of a preselected ion in the dialysis liquid for the calculation and/or control of the corresponding ion content in the blood.

11. The dialysis system in accordance with claim 1, wherein said measuring means comprises a gas analyzer for the measurement of the gas content in the dialysis liquid for the calculation and/or control of the corresponding gas content in the blood.

12. The dialysis system in accordance with claim 1, further including composition controlling means for controlling the composition of the dialysis liquid on the dialysis liquid input side of said dialyzer as a function of the parameter being measured by said measuring means, whereby the operation of said control means is a direct function of the control of a corresponding blood parameter.

13. The dialysis system in accordance with claim 12, wherein said composition controlling means is operative for the adjustment of the composition of the dialysis liquid before the dialyzer to bring about an equilibrium between the conductivity in the dialysis liquid and in the blood.

14. The dialysis system in accordance with claim 13, wherein the blood conductivity corresponds to the ion concentration in the blood selected from the group consisting of sodium ions, potassium ions and calcium ions.

15. The dialysis system in accordance with claim 1, further including means for measuring the value of at least one of said parameters of the dialysis liquid on the dialysis liquid input side of said dialyzer, and by pass means for bypassing fresh dialysis liquid passed said dialyzer and directly to said measuring means on the dialysis liquid output side of said dialyzer for the calibration thereof.

16. The dialysis system in accordance with claim 1, further including means for measuring the value of at least one of said parameters of said dialysis liquid on the dialysis liquid input side of said dialyzer, said comparison means for comparing the values of the measured parameter before and after said dialyzer for the calculation and/or control of the corresponding parameter in the blood.

* * * * *